United States Patent
Scanlan et al.

(10) Patent No.: US 11,613,517 B2
(45) Date of Patent: Mar. 28, 2023

(54) AMIDE PRODRUGS OF SMALL MOLECULE NUCLEAR RECEPTOR MODULATORS

(71) Applicant: OREGON HEALTH & SCIENCE UNIVERSITY, Portland, OR (US)

(72) Inventors: Thomas S. Scanlan, Portland, OR (US); Skylar J. Ferrara, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 2 days.

(21) Appl. No.: 16/971,171

(22) PCT Filed: Feb. 26, 2019

(86) PCT No.: PCT/US2019/019576
§ 371 (c)(1),
(2) Date: Aug. 19, 2020

(87) PCT Pub. No.: WO2019/168842
PCT Pub. Date: Sep. 6, 2019

(65) Prior Publication Data
US 2021/0087137 A1 Mar. 25, 2021

Related U.S. Application Data

(60) Provisional application No. 62/637,884, filed on Mar. 2, 2018.

(51) Int. Cl.
| C07C 235/34 | (2006.01) |
| C07C 235/20 | (2006.01) |
| C07C 233/65 | (2006.01) |
| C07C 233/25 | (2006.01) |
| C07C 233/05 | (2006.01) |
| C07C 309/66 | (2006.01) |
| C07C 309/41 | (2006.01) |
| C07D 261/20 | (2006.01) |
| C07D 277/26 | (2006.01) |
| C07D 409/06 | (2006.01) |
| A61P 25/00 | (2006.01) |

(52) U.S. Cl.
CPC .......... *C07C 235/34* (2013.01); *C07C 233/65* (2013.01); *C07C 309/66* (2013.01); *C07D 261/20* (2013.01); *C07D 277/26* (2013.01); *C07D 409/06* (2013.01); *C07C 2602/10* (2017.05)

(58) Field of Classification Search
CPC ... C07C 235/34; C07C 235/20; C07C 233/65; C07C 233/25; C07C 233/05; C07C 309/66; C07C 309/41; C07C 2602/10; C07D 261/20; C07D 277/26; C07D 409/06; A61P 25/00; A61P 31/423; A61P 31/426; A61P 31/4436
See application file for complete search history.

(56) References Cited

U.S. PATENT DOCUMENTS

| 3,845,770 | A | 11/1974 | Theeuwes et al. |
| 4,326,525 | A | 4/1982 | Swanson et al. |
| 4,741,897 | A | 5/1988 | Andrews et al. |
| 4,992,445 | A | 2/1991 | Lawter et al. |
| 5,001,139 | A | 3/1991 | Lawter et al. |
| 5,023,252 | A | 6/1991 | Hseih et al. |
| 5,616,345 | A | 4/1997 | Geoghegan et al. |
| 9,562,012 | B2 | 2/2017 | Tanis et al. |
| 10,233,197 | B2 | 3/2019 | Yu |
| 2009/0105347 | A1 | 4/2009 | Scanlan et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1* | 9/2014 | Fujii .................. C07F 15/0093 564/171 |
| 2017/0007589 | A1 | 1/2017 | Ding et al. |
| 2017/0226154 | A1 | 8/2017 | Evans et al. |

FOREIGN PATENT DOCUMENTS

| CN | 101547898 A | 9/2009 |
| RU | 2144913 C1 | 1/2000 |
| WO | 9321146 A1 | 10/1993 |
| WO | 02081426 A1 | 10/2002 |
| WO | 2004043939 A1 | 5/2004 |
| WO | 2013006734 A1 | 1/2013 |
| WO | 2015188015 A1 | 12/2015 |

OTHER PUBLICATIONS

Clark et al., Expert Opinion on Drug Metabolism and Toxicology, 2020, vol. 16, 1097-1108.*
EP19759941.8 , "Extended European Search Report", dated Feb. 10, 2022, 10 pages.
CN201980016157.4, "Office Action", dated Apr. 8, 2021, 9 pages.
EP19759941.8, "Partial Supplementary European Search Report", dated Nov. 9, 2021, 12 pages.
Martin et al., "The Proliferating Cell Nuclear Antigen Regulates Retinoic Acid Receptor Transcriptional Activity Through Direct Protein-Protein Interaction", Nucleic Acids Research, vol. 33, Issue 13, Jul. 2005, pp. 4311-4321.
PCT/US2019/019576, "International Preliminary Report on Patentability", dated Sep. 17, 2020, 6 pages.
CN201980016157.4, "Notice of Decision to Grant", dated Oct. 9, 2021, 2 pages.
Actis et al., "Small Molecule Inhibitors of PCNA/PIP-Box Interaction Suppress Translesion DNA Synthesis", Bioorganic & Medicinal Chemistry, vol. 21, Issue 7, Apr. 1, 2013, pp. 1972-1977.

(Continued)

*Primary Examiner* — Sun Jae Yoo

(74) *Attorney, Agent, or Firm* — Kilpatrick Townsend & Stockton LLP

(57) ABSTRACT

Provided herein are novel amide prodrug forms of pharmaceutically active agents useful for central nervous system disorders.

3 Claims, 9 Drawing Sheets

(56) References Cited

OTHER PUBLICATIONS

PCT/US2019/019576, International Search Report and Written Opinion, dated May 13, 2019, 8 pages.
Placzek et al., "New Synthetic Routes to Thyroid Hormone Analogs: d6-Sobetirome, 3H-Sobetirome, and the Antagonist NH-3", Tetrahedron, vol. 71, No. 35, Sep. 2, 2015, pp. 5946-5951.
IN202017036645, "First Examination Report", Mar. 25, 2022, 5 pages.
MX/A/2020/008972, "Office Action", dated Aug. 9, 2022, 4 pages.
RU2020132293, "Office Action", dated Aug. 24, 2022, 17 pages.
IL276892, "Office Action", dated Jun. 22, 2022, 4 pages.

* cited by examiner

Brain

Serum

Brain

Serum

Brain

Serum

AMIDE PRODRUGS OF SMALL MOLECULE NUCLEAR RECEPTOR MODULATORS

CROSS REFERENCE TO RELATED APPLICATIONS

This application is a National Stage Application of International Application No. PCT/US2019/019576 filed Feb. 26, 2019, which claims priority to U.S. Provisional Application No. 62/637,884 filed Mar. 2, 2018, the contents of which are incorporated by reference in their entireties.

STATEMENT AS TO RIGHTS TO INVENTIONS MADE UNDER FEDERALLY SPONSORED RESEARCH AND DEVELOPMENT

This invention was made with government support under R01 DK052798 awarded by the National Institutes of Health. The government has certain rights in the invention.

The present invention relates to novel amide prodrug forms of Central Nervous System drugs with enhanced ability to complete blood-brain barrier passage.

BACKGROUND OF THE INVENTION

Nuclear receptor modulators include receptors for steroid hormones, lipophilic vitamins, sterols, and bile acids are targets for an important class of therapeutics of great therapeutic interest, encompassing 10-15% of the new drugs approved by the U.S. Food and Drug Administration. Among the most significant areas of interest are central nervous system disorders, including Alzheimer's Disease, Parkinson's Disease, demylenation disorders, and glioblastomas.

While nuclear receptor modulators exhibit potent therapeutic effects, many also feature deleterious effects from receptor engagement in the periphery. There remains a need for therapeutic compounds with blood-brain barrier passage ability.

SUMMARY OF THE INVENTION

Provided herein are novel amide prodrugs of pharmaceutically active compounds useful in the treatment of central nervous system (CNS) disorders.

Most nuclear receptor ligands are non-polar small molecules with functional groups for target engagement with the desired receptor. A common functional group is the carboxylic acid, which at physiological pH is deprotonated as the carboxylate, and carboxylates (along with phosphates) are the strongest hydrogen bond acceptors and their persistent negative charge forms strong electrostatic interactions with the receptor. However, their persistent negative charge is a serious liability for crossing the blood brain barrier due to charge repulsion at the surface of the barrier. On the other hand, the most recent potent modulators have isosteric replacement of the carboxylate for other functional groups that allow passage through the barrier—however, they are equipotent all over the body, and fail in the clinic due to specific adverse effects in the periphery.

Provided herein are amide derivatives of active pharmaceutical agents, or a pharmaceutically acceptable salt thereof, capable of delivering active agents to the CNS, particularly including the brain.

DETAILED DESCRIPTION OF THE INVENTION

Figure 1:
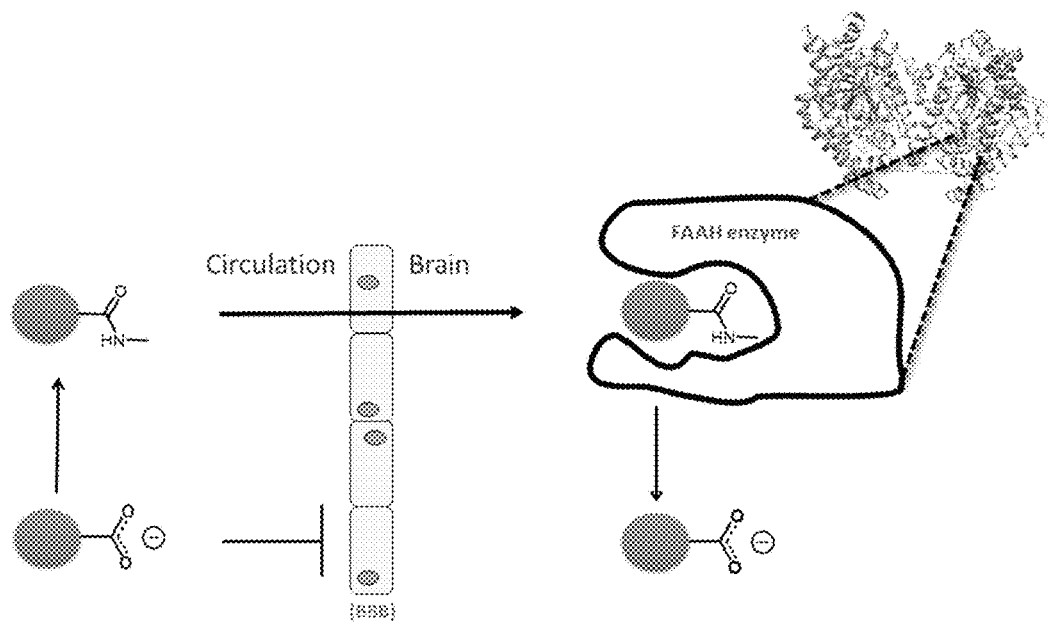
FIG. 1 depicts amide prodrug forms of potent nuclear receptor modulating compounds successfully passing the Blood-Brain Barrier before conversion to active pharmaceutical agent.
Figure 2A:
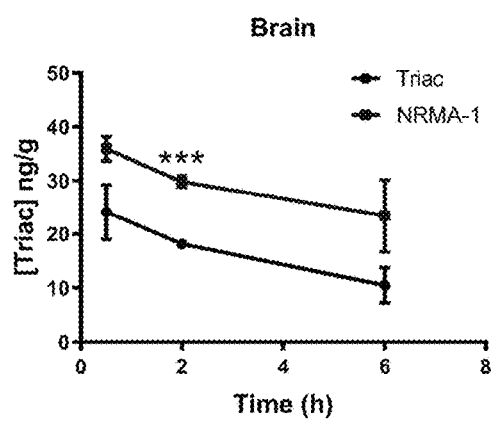
FIGS. 2A and 2B represent individual brain (A) and serum (B) AUC comparisons for NH3 and NMRA-2 identified after administration in mouse brain and serum.
Figure 2B:
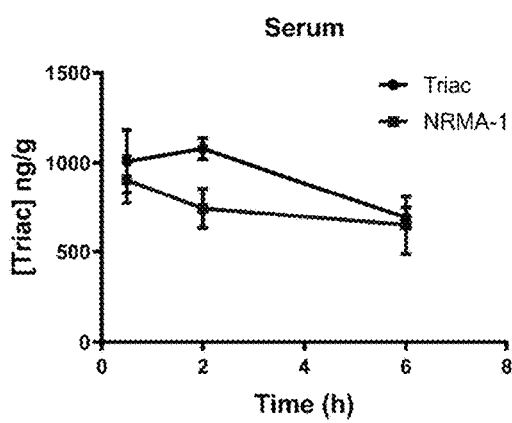
Figure 3A:
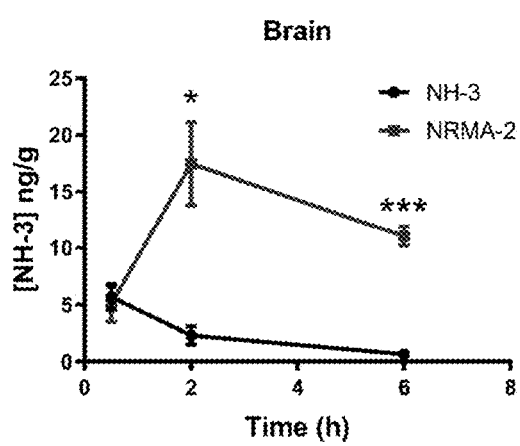
FIGS. 3A and 3B represent individual brain (A) and serum (B) AUC comparisons for Triac and NMRA-1 identified after administration in mouse brain and serum.
Figure 3B:
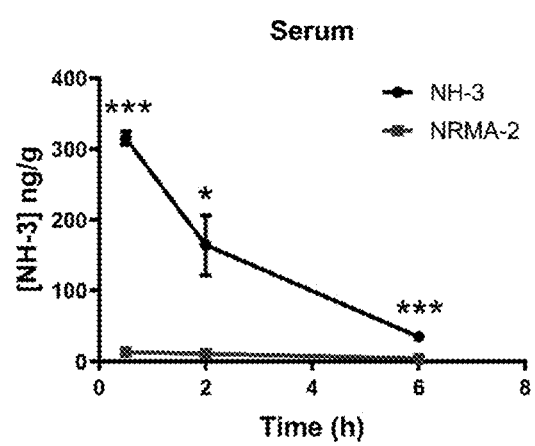
Figure 4A:
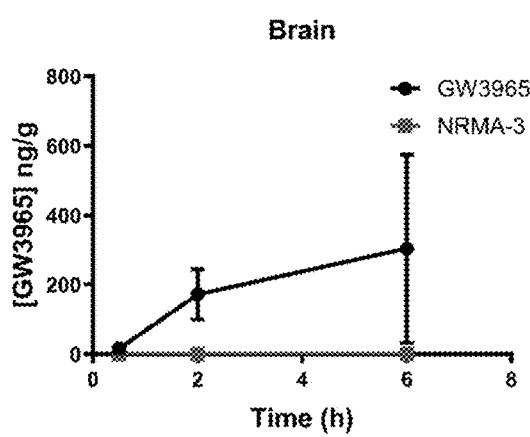
FIGS. 4A and 4B represent individual brain (A) and serum (B) AUC comparisons for GW3965 and NMRA-3 identified after administration in mouse brain and serum.
Figure 4B:
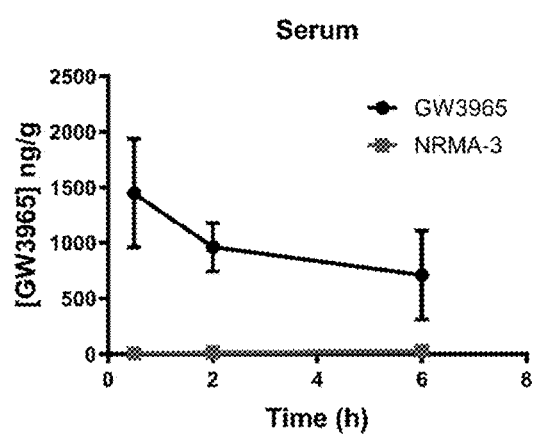
Figure 5A:
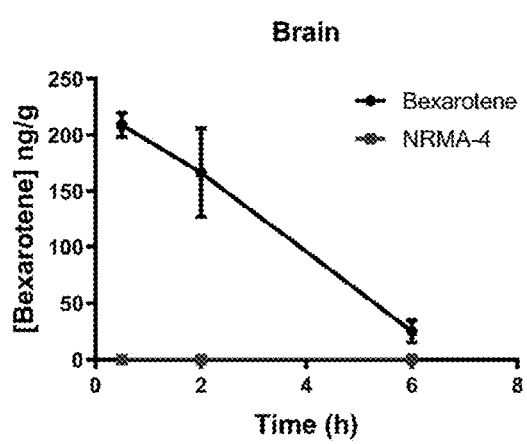
FIGS. 5A and 5B represent individual brain (A) and serum (B) AUC comparisons for Bexarotene and NMRA-4 identified after administration in mouse brain and serum.
Figure 5B:
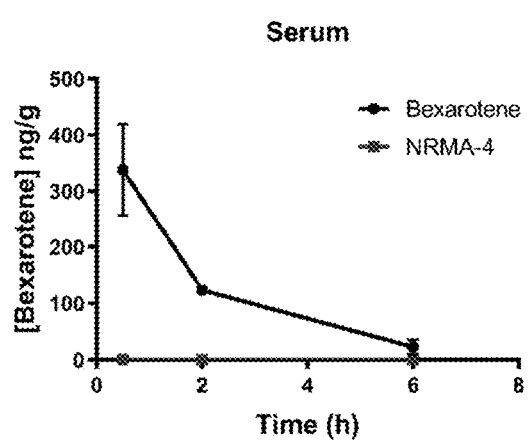
Figure 6A:
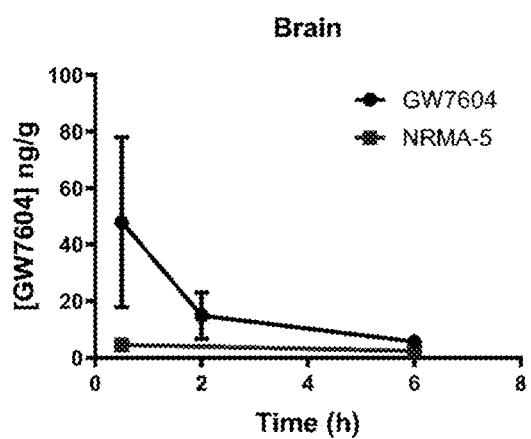
FIGS. 6A and 6B represent individual brain (A) and serum (B) AUC comparisons for GW7604 and NMRA-5 identified after administration in mouse brain and serum.
Figure 6B:
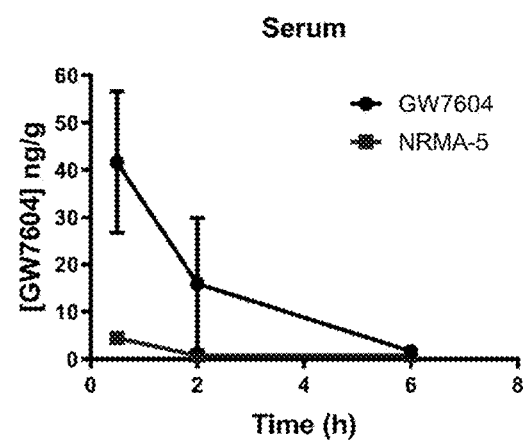
Figure 7A:
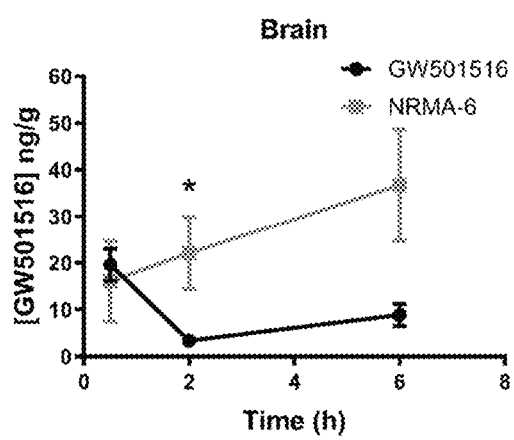
FIGS. 7A and 7B represent individual brain (A) and serum (B) AUC comparisons for GW501516 and NMRA-6 identified after administration in mouse brain and serum.
Figure 7B:
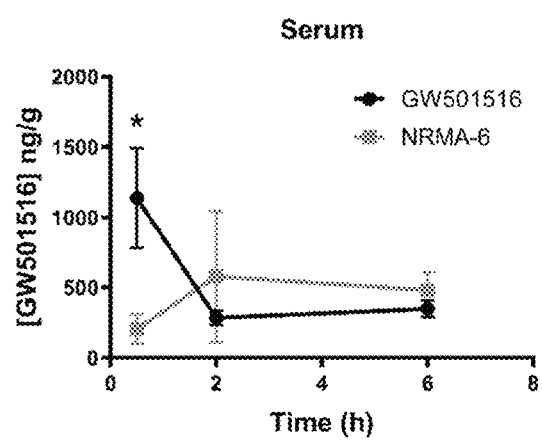
Figure 8A:
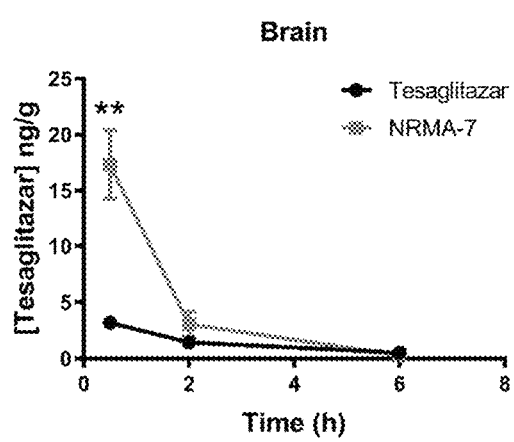
FIGS. 8A and 8B represent individual brain (A) and serum (B) AUC comparisons for Tesagliazar and NMRA-7 identified after administration in mouse brain and serum.
Figure 8B:
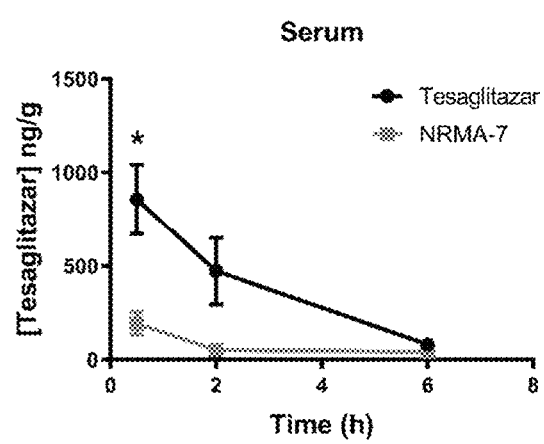
Figure 9A:
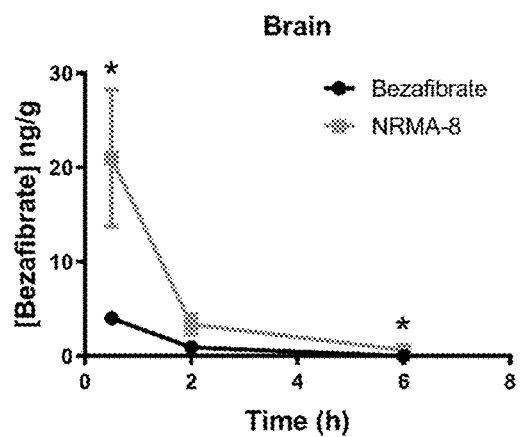
FIGS. 9A and 9B represent individual brain (A) and serum (B) AUC comparisons for Bezafibrate and NMRA-8 identified after administration in mouse brain and serum.
Figure 9B:
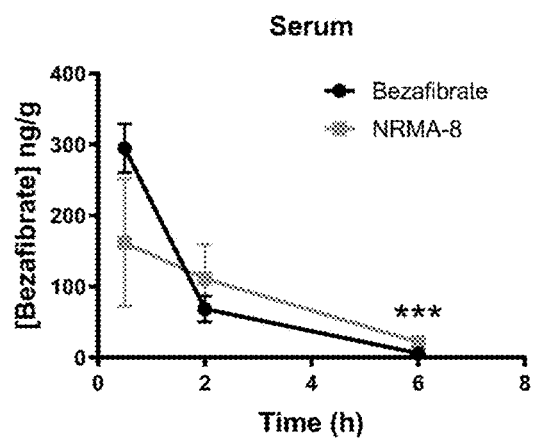
Figure 10A:
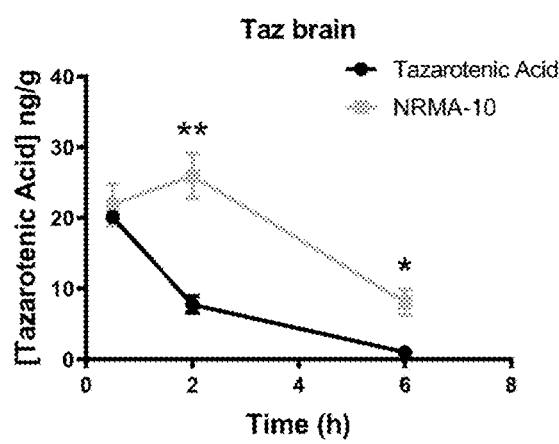
FIGS. 10A and 10B represent individual brain (A) and serum (B) AUC comparisons for Tazarotenic Acid and NMRA-10 identified after administration in mouse brain and serum.
Figure 10B:
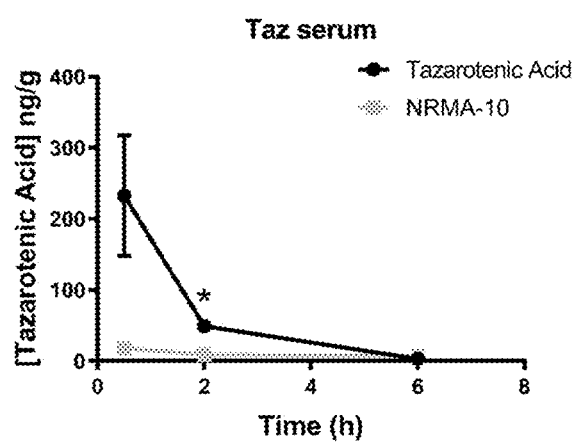
Figure 11A:
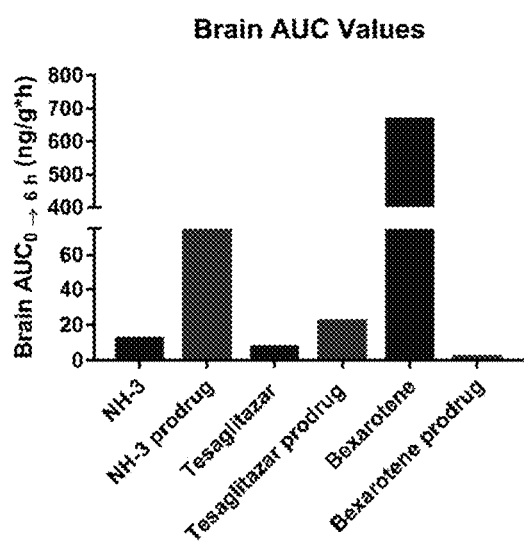
FIGS. 11A and 11B depict the Brain AUCs (A) and Brain/Serum Ratios (B) of three drugs and their corresponding methyl amide prodrug.
Figure 11B:
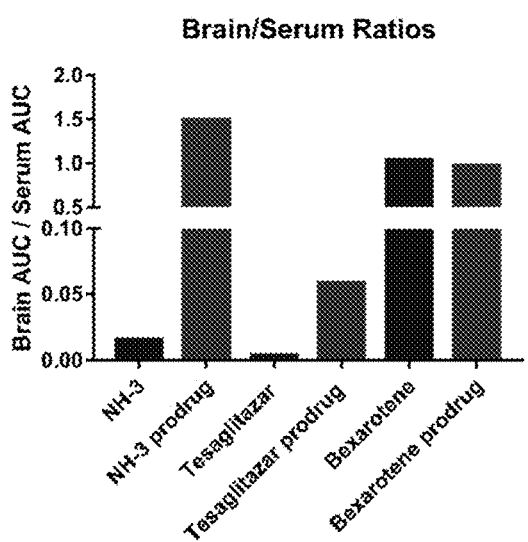
Figure 12:
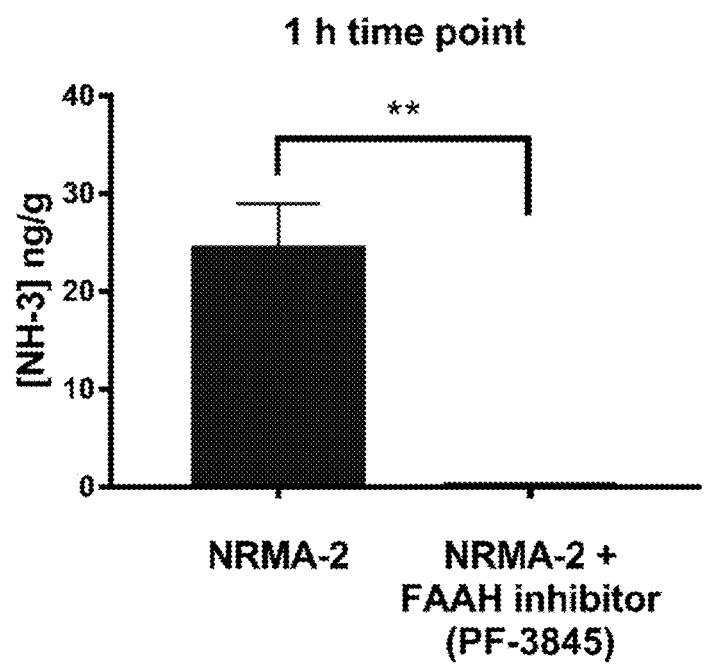
FIG. 12 depicts in vivo validation that NH-3 prodrug is a substrate for the FAAH enzyme.
Figure 13:
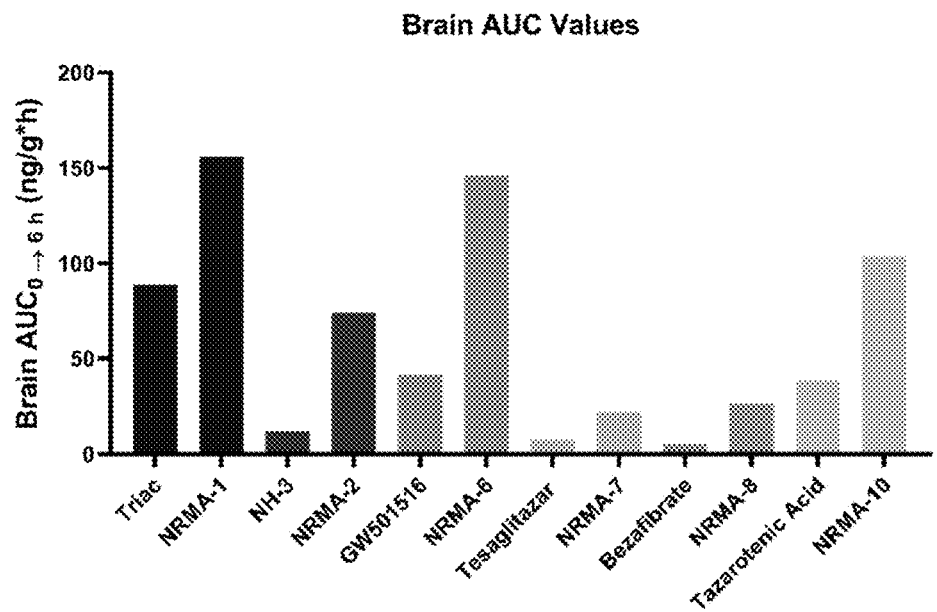
FIG. 13 depicts comparison of brain AUC values for tested compounds.
Figure 14:
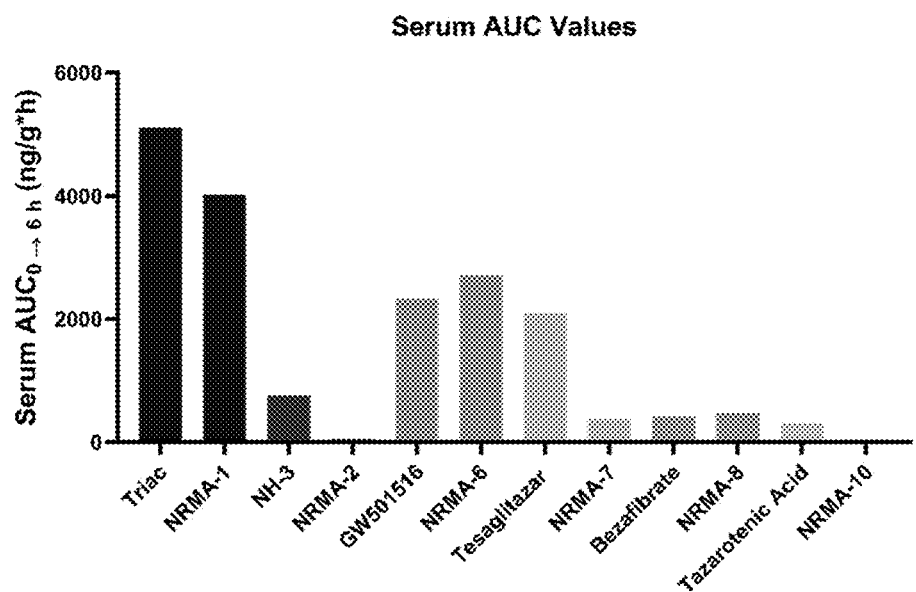
FIG. 14 depicts comparison of serum AUC values for tested compounds.
Figure 15:
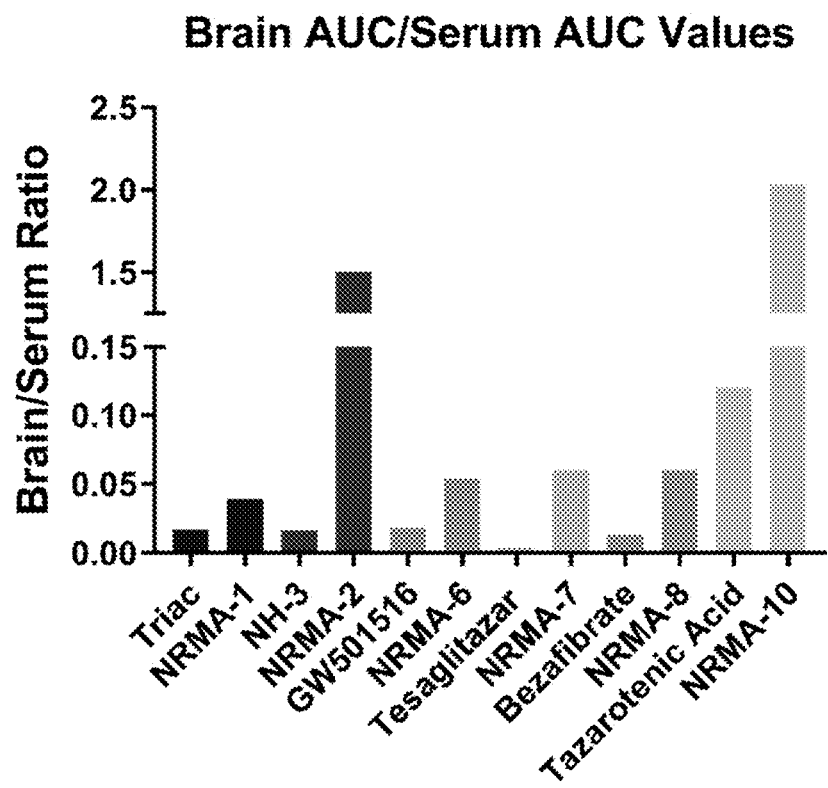
FIG. 15 represents brain/serum AUC ratios for tested compounds.

An embodiment provides amide analogs of Tiratricol, also known as Triac, Triacana, and 2-(4-(4-hydroxy-3-iodophenoxy)-3,5-diiodophenyl)acetic acid, or a pharmaceutically acceptable salt thereof, having the structure:

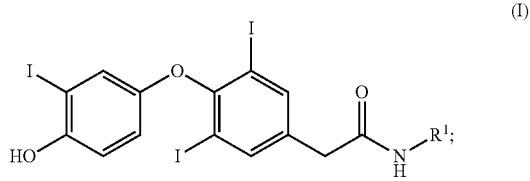

(I)

wherein $R^1$ is a $C_1$-$C_4$ linear or branched alkyl.

An example of the amides in this group is 2-(4-(4-hydroxy-3-iodophenoxy)-3,5-diiodophenyl)-N-methylacetamide, structure below, also referred to herein as NRMA-1, or a pharmaceutically acceptable salt thereof.

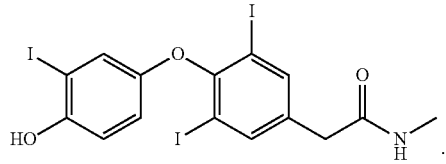
(II)

The amide prodrugs of Formulas (I) and (II) above are useful in methods of treatment for neurodegenerative disorders, including motor neuron defects, amyotrophic lateral sclerosis, multiple sclerosis, spinal cord injury, demyelinating diseases, and myelopathies. Each individual method comprises administering to a subject in need thereof a pharmaceutically effective amount of a compound of Formula (I), or a pharmaceutically acceptable salt thereof.

An embodiment provides amide analogs of NH-3, also known as NH 3 (receptor antagonist) and 2-(4-(4-hydroxy-3-isopropyl-5-((4-nitrophenyl)ethynyl)benzyl)-3,5-dimethylphenoxy)acetic acid, or a pharmaceutically acceptable salt thereof, having the structure:

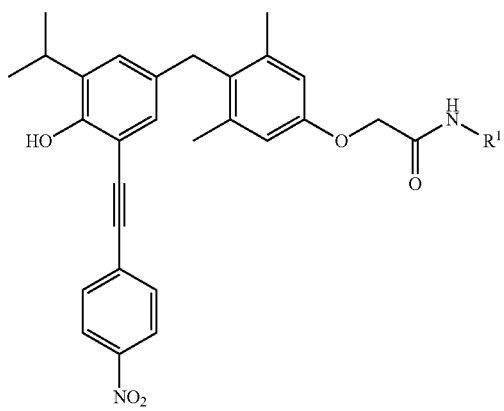
(III)

wherein $R^1$ is a $C_1$-$C_4$ linear or branched alkyl.

An example of amides in this group include 2-(4-(4-hydroxy-3-isopropyl-5-((4-nitrophenyl)ethynyl)benzyl)-3,5-dimethylphenoxy)-N-methylacetamide, structure below, also referred to herein as NRMA-2, or a pharmaceutically acceptable salt thereof.

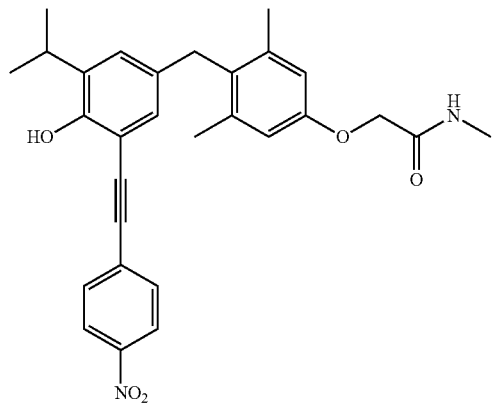
(IV)

The amide prodrugs of Formulas (III) and (IV) above are useful in methods of treatment for neurodegenerative disorders, including motor neuron defects, amyotrophic lateral sclerosis, multiple sclerosis, spinal cord injury, demyelinating diseases, and myelopathies. Each individual method comprises administering to a subject in need thereof a pharmaceutically effective amount of a compound of Formula (III), or a pharmaceutically acceptable salt thereof.

Another embodiment provides amide analogs of Eprotirome, also known as KB2115 and 3-((3,5-dibromo-4-(4-hydroxy-3-isopropylphenoxy)phenyl)amino)-3-oxopropanoic acid, or a pharmaceutically acceptable salt thereof, having the structure:

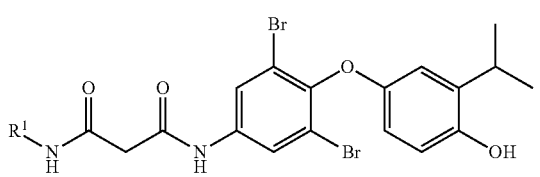
(V)

wherein $R^1$ is a $C_1$-$C_4$ linear or branched alkyl.

An example of amides in the group above is N1-(3,5-dibromo-4-(4-hydroxy-3-isopropylphenoxy)phenyl)-N3-methylmalonamide, structure below, or a pharmaceutically acceptable salt thereof.

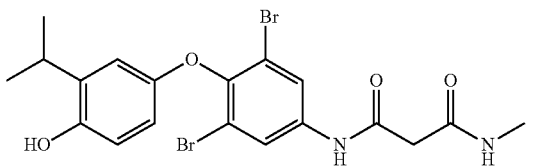
(VI)

The amide prodrugs of Formulas (V) and (VI) above are useful in methods of treatment for neurodegenerative disorders, including motor neuron defects, amyotrophic lateral sclerosis, multiple sclerosis, spinal cord injury, demyelinating diseases (including Multiple Sclerosis), and myelopathies. Each individual method comprises administering to a subject in need thereof a pharmaceutically effective amount of a compound of Formula (V), or a pharmaceutically acceptable salt thereof.

A further embodiment provides amide analogs of Bexarotene, or a pharmaceutically acceptable salt thereof, having the structure:

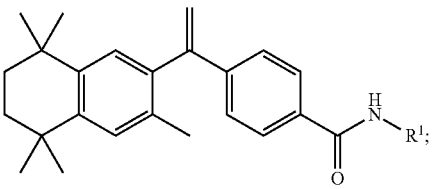
(VII)

wherein $R^1$ is a $C_1$-$C_4$ linear or branched alkyl.

A specific example of these compounds is N-methyl-4-(1-(3,5,5,8,8-pentamethyl-5,6,7,8-tetrahydronaphthalen-2- yl)vinyl)benzamide, structure below, also referred to herein as NRMA-4, or a pharmaceutically acceptable salt thereof.

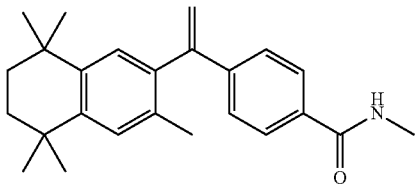
(VIII)

The amide prodrugs of Formulas (VII) and (VIII) above are useful in methods of treatment for neurodegenerative disorders including Alzheimer's Disease and Parkinson's Disease, including motor neuron defects, amyotrophic lateral sclerosis, multiple sclerosis, spinal cord injury, demyelinating diseases, and myelopathies. Each individual method comprises administering to a subject in need thereof a pharmaceutically effective amount of a compound of Formula (VII), or a pharmaceutically acceptable salt thereof.

A further embodiment provides amide analogs of GW7064, also known as (E)-3-(4-((E)-1-(4-hydroxyphenyl)-2-phenylbut-1-en-1-yl)phenyl)acrylic acid, or a pharmaceutically acceptable salt thereof, having the structure:

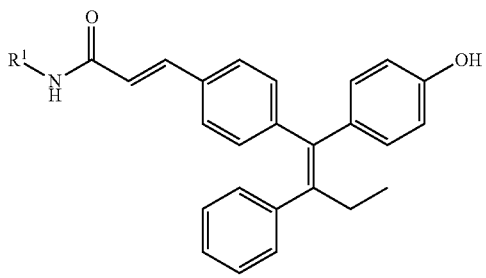
(IX)

wherein $R^1$ is a $C_1$-$C_4$ linear or branched alkyl.

An example of a compound from this group is (E)-3-(4-((E)-1-(4-hydroxyphenyl)-2-phenylbut-1-en-1-yl)phenyl)-N-methylacrylamide, structure below, also referred to herein as NRMA-5, or a pharmaceutically acceptable salt thereof.

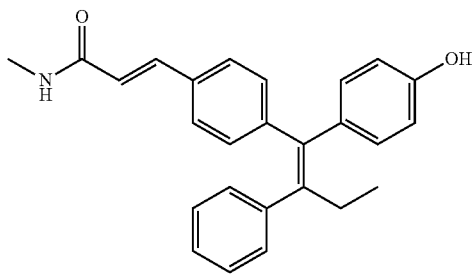
(X)

The amide prodrugs of Formulas (IX) and (X) above are useful in methods of treatment for metastatic breast cancer in the central nervous system, including the brain. Each individual method comprises administering to a subject in need thereof a pharmaceutically effective amount of a compound of Formula (IX), or a pharmaceutically acceptable salt thereof.

A further embodiment provides amide analogs of GW3965, also known GW3965A and 2-(3-(3-((2-chloro-3-(trifluoromethyl)benzyl)(2,2-diphenylethyl)amino)propoxy)phenyl)-N-methylacetamide, or a pharmaceutically acceptable salt thereof, having the structure:

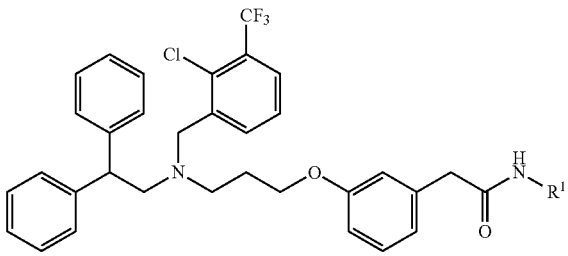
(XI)

wherein $R^1$ is a $C_1$-$C_4$ linear or branched alkyl.

An example of compounds of this group is 2-(3-(3-((2-chloro-3-(trifluoromethyl)benzyl)(2,2-diphenylethyl)amino)propoxy)phenyl)-N-methylacetamide, structure below, also referred to herein as NMRA-3, or a pharmaceutically acceptable salt thereof.

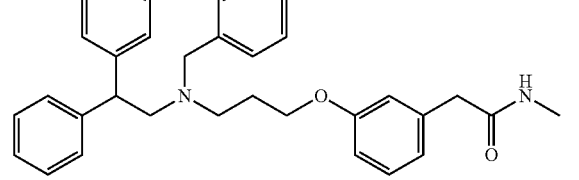
(XII)

The amide prodrugs of Formulas (XI) and (XII) above are useful in methods of treatment for neurodegenerative disorders including Parkinson's Disease, Huntington's Disease, age-related macular degeneration (AMD), and dementias, including dementia with Lewy bodies (DLB), synucleinopathies, dyskinesia, (including bradykinesia, akinesia and dystonia), Alzheimer's disease (AD), multiple system atrophy (MSA) including Shy-Drager syndrome, pure autonomic failure (PAF), or Pick disease (PiD). Each individual method comprises administering to a subject in need thereof a pharmaceutically effective amount of a compound of Formula (VII), or a pharmaceutically acceptable salt thereof.

Also useful are amide prodrugs of PPAR modulators, including those below.

In one embodiment, the compounds are analogs of Tesaglitazar having the structure:

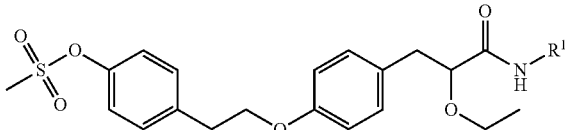
(XIII)

wherein $R^1$ is a $C_1$-$C_4$ linear or branched alkyl; or a pharmaceutically acceptable salt thereof.

An example of this group includes the compound (S)-4-(2-(4-(2-ethoxy-3-(methylamino)-3-oxopropyl)phenoxy)ethyl)phenyl methanesulfonate, structure below, also referred to herein as NMRA-7, or a pharmaceutically acceptable salt thereof.

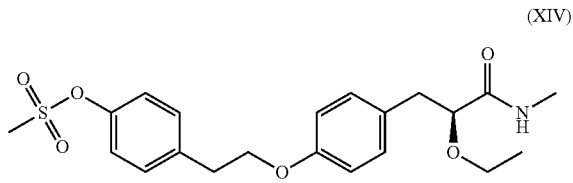

(XIV)

A further embodiment provides amide analogs of GW501516, also known GW1516 and 2-(2-methyl-4-(((4-methyl-2-(4-(trifluoromethyl)phenyl)thiazol-5-yl)methyl)thio)phenoxy)acetic acid, or a pharmaceutically acceptable salt thereof, having the structure:

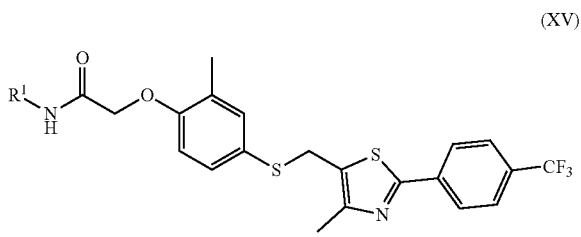

(XV)

wherein R¹ is a $C_1$-$C_4$ linear or branched alkyl.

An example of compounds of this group is N-methyl-2-(2-methyl-4-(((4-methyl-2-(4-(trifluoromethyl)phenyl)thiazol-5-yl)methyl)thio)phenoxy)acetamide, structure below, also referred to herein as NRMA-6, or a pharmaceutically acceptable salt thereof.

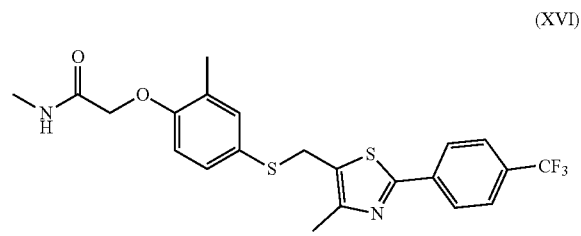 [SMILES: CNC(=O)COc1ccc(SCc2sc(-c3ccc(C(F)(F)F)cc3)nc2C)cc1C]

(XVI)

In still another embodiment the compounds are analogs of Bezafibrate, also known as BM 15075, Befizal, Benzofibrate, and 2-[4-[2-[(4-chlorobenzoyl)amino]ethyl]phenoxy]-2-methyl-propanoic acid, having the structure:

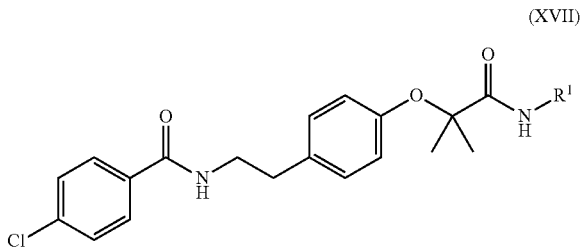

(XVII)

wherein R¹ is a $C_1$-$C_4$ linear or branched alkyl; or a pharmaceutically acceptable salt thereof.

An example of an amide prodrug from this group includes 4-chloro-N-(4-((2-methyl-1-(methylamino)-1-oxopropan-2-yl)oxy)phenethyl)benzamide, structure below, also referred to herein as NMRA-8, or a pharmaceutically acceptable salt form thereof.

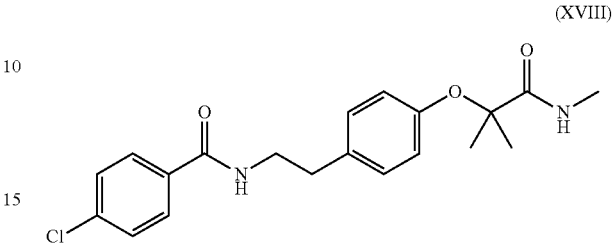

(XVIII)

The amide prodrugs of Formulas (XIII), (XIV), (XV), (XVI), (XVII), and (XVIII), above are useful in methods of treatment for neurodegenerative disorders including Alzheimer's Disease and Parkinson's Disease, Pick's disease, including motor neuron defects, amyotrophic lateral sclerosis, multiple sclerosis, spinal cord injury, demyelinating diseases, myelopathies, and glioblastomas. Each individual method comprises administering to a subject in need thereof a pharmaceutically effective amount of a compound of selected from those of the group of Formulas (XIII), (XIV), (XV), (XVI), (XVII), and (XVIII), or a pharmaceutically acceptable salt thereof.

In each of the embodiments above, the compounds are defined as R¹ comprising $C_1$-$C_4$ linear or branched alkyl, indicating an alkyl group of 1, 2, 3, or 4 carbon atoms. This is understood to include linear methyl, ethyl, propyl, and butyl groups, as well as isopropyl, isobutyl, sec-butyl, and tert-butyl branched alkyl chains. In a separate embodiment within each of the embodiments above comprises the compounds depicted wherein R¹ is $C_1$-$C_3$ linear or branched alkyl, or a pharmaceutically acceptable salt thereof. In another separate embodiment within each of the embodiments above comprises the compounds depicted wherein R¹ is selected from methyl and ethyl, or a pharmaceutically acceptable salt thereof.

Also provided are separate pharmaceutical compositions comprising a pharmaceutically effective amount of each of the compound groups and individual compounds above of Formulas (I) through (XVIII), or a pharmaceutically acceptable salt thereof, and a pharmaceutically acceptable carrier or excipient.

Also provided is the use of a compound selected from any of Formulas (I) through (XVIII), or a pharmaceutically acceptable salt thereof, in the preparation of a medicament.

Synthetic Scheme

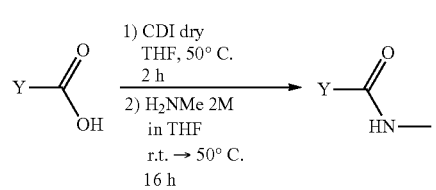

A modular synthesis of prodrug N-methyl amides was developed. Activation of the parent drug carboxylic acid with carbonyldiimidazole (CDI) followed by the addition of excess methylamine in THF provides the N-methyl amide prodrugs in moderate-to-good yields. The advantage of this method relates to the mild conditions for amide coupling of these rather expensive parent drug starting materials, which typically generates product mixtures that are only amide product and starting material.

Parent Drug Abbreviations

All parent drugs were purchased from commercial sources with the exception of NH-3 which was synthesized in our laboratory.[1]

1) Placzek, A. T., and Scanlan, T. S. (2015) New synthetic routes to thyroid hormone analogs: d6-sobetirome, 3H-sobetirome, and the antagonist NH-3. *Tetrahedron* 71, 5946-5951.

Triac (also known as tiratricol and Triacana)=2-(4-(4-hydroxy-3-iodophenoxy)-3,5-diiodophenyl)acetic acid

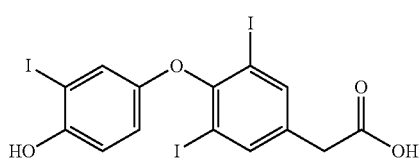 [SMILES: O=C(O)Cc1cc(I)c(Oc2ccc(O)c(I)c2)c(I)c1]

NH-3=2-(4-(4-hydroxy-3-isopropyl-5-((4-nitrophenyl)ethynyl)benzyl)-3,5-dimethylphenoxy)acetic acid

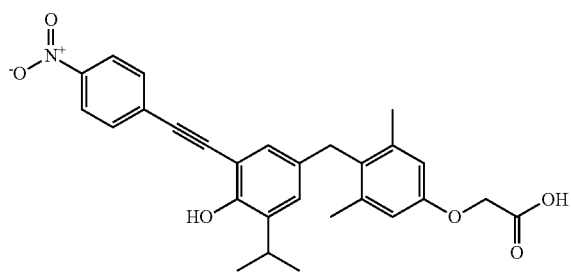

GW3965=2-(3-(3-((2-chloro-3-(trifluoromethyl)benzyl)(2,2-diphenylethyl)amino)propoxy)phenyl)acetic acid

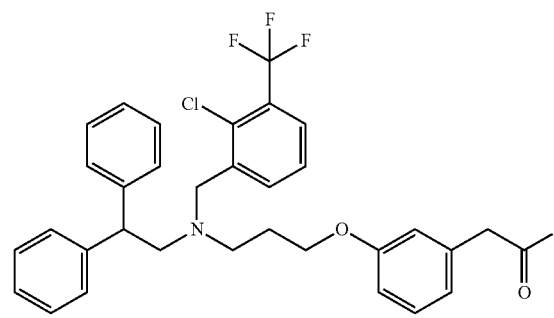

Bexarotene=4-(1-(3,5,5,8,8-pentamethyl-5,6,7,8-tetrahydronaphthalen-2-yl)vinyl)benzoic acid

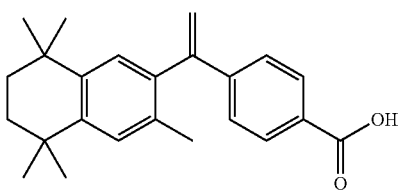 [SMILES: C=C(c1ccc(C(=O)O)cc1)c1cc2c(cc1C)C(C)(C)CCC2(C)C]

GW7604=(E)-3-(4-((E)-1-(4-hydroxyphenyl)-2-phenylbut-1-en-1-yl)phenyl)acrylic acid

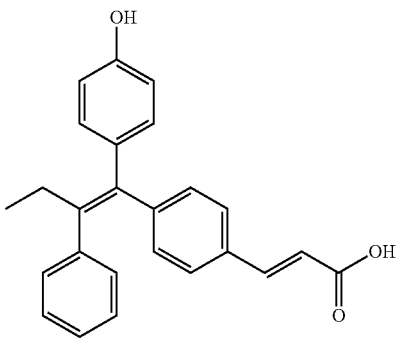 [SMILES: CC/C(=C(\c1ccc(O)cc1)c1ccc(/C=C/C(=O)O)cc1)c1ccccc1]

GW501516=2-(2-methyl-4-(((4-methyl-2-(4-(trifluoromethyl)phenyl)thiazol-5-yl)methyl)thio)phenoxy)acetic acid

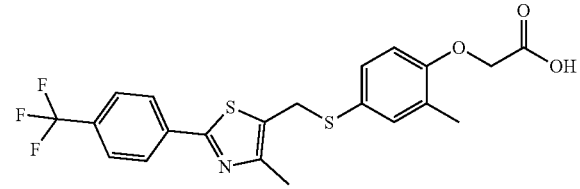 [SMILES: Cc1cc(SCc2sc(-c3ccc(C(F)(F)F)cc3)nc2C)ccc1OCC(=O)O]

Tesaglitazar=(S)-2-ethoxy-3-(4-(4-((methylsulfonyl)oxy)phenethoxy)phenyl)propanoic acid

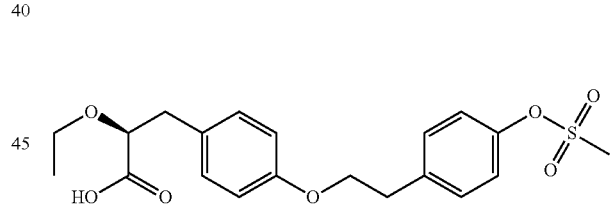

Bezafibrate=2-(4-(2-(4-chlorobenzamido)ethyl)phenoxy)-2-methylpropanoic acid

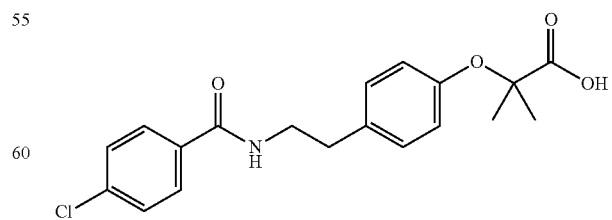

F3MethylAA=2-(3-chloro-4-((3-((7-propyl-3-(trifluoromethyl)benzo[d]isoxazol-6-yl)oxy)propyl)thio)phenyl)acetic acid

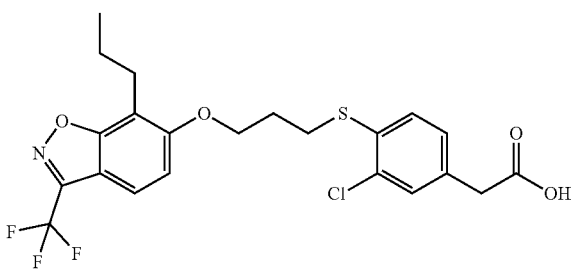 [SMILES: CCCc1c(OCCCSc2ccc(CC(=O)O)cc2Cl)ccc2c(C(F)(F)F)noc12]

Tazarotenic acid=6-(4,4-dimethylthiochroman-6-yl)ethynyl)nicotinic acid

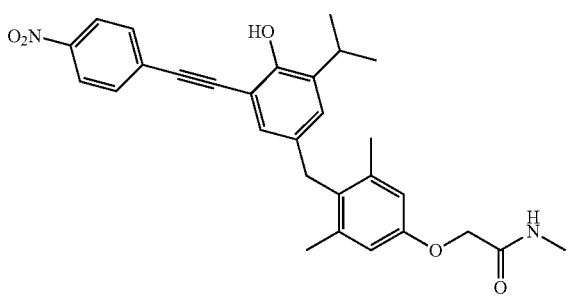

NRMA-2

2-(4-(4-hydroxy-3-isopropyl-5-((4-nitrophenyl)ethynyl)benzyl)-3,5-dimethylphenoxy)-N-methylacetamide 35 mg NH-3 (0.074 mmol) yielded 18.7 mg (0.038 mmol, 52%) product as a yellow powder.

$^1$H NMR (400 MHz, Chloroform-d) δ 8.24 (d, J=8.9 Hz, 2H), 7.65 (d, J=8.9 Hz, 2H), 7.04 (s, 1H), 6.74 (s, 1H), 6.67 (s, 2H), 5.77 (s, 1H), 4.52 (s, 2H), 3.93 (s, 2H), 3.29 (septet, 1H), 2.94 (d, J=5.0 Hz, 3H), 2.26 (s, 6H), 1.26 (t, J=6.1 Hz, 6H). HRMS (ESI) m/z [M+1]$^+$ $C_{29}H_{31}N_2O_5^+$ requires 487.2227, found 487.2225.

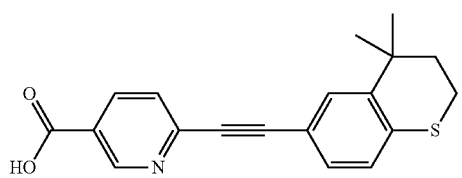 [SMILES: CC1(C)CCSc2ccc(C#Cc3ccc(C(=O)O)cn3)cc21]

Experimental

General Synthetic Procedure:

35 mg (1 equivalent) of parent drug carboxylic acid was placed in a thick-walled tube containing carbonyldiimidazole (CDI, 1.2 equivalents), a stir bar, and 3 mL of dry THF. The tube was sealed, placed under vacuum, then refilled with argon three times. While under argon, the mixture was heated for 2 h at 50° C. then cooled to room temperature. Three additional vacuum/argon refills were performed followed by the addition of excess methylamine (~10 equivalents, 2M in THF) via syringe. The mixture was stirred at room temperature for 2 h, then heated to 50° C. for ~14 h. Upon cooling, the product mixture was diluted with dichloromethane and washed with 1N HCl and brine. All organic layers were combined, dried with sodium sulfate, and evaporated to dryness to give the crude product mixture typically containing only starting material and product. The product was separated on silica with 1-10% MeOH in DCM usually as the first band.

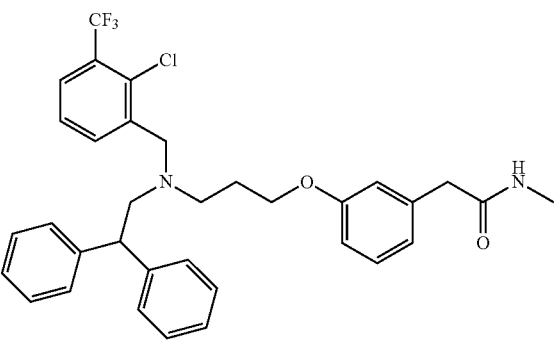

NRMA-3

2-(3-(3-((2-chloro-3-(trifluoromethyl)benzyl)(2,2-diphenylethyl)amino)propoxy)phenyl)-N-methylacetamide 35 mg GW3965 (0.06 mmol) yielded 13.6 mg (0.023 mmol, 38%) product as a colorless residue. Note: during workup, the crude reaction mixture was washed with 0.5M NaOH(aq) and separated on column to give the charge neutral species.

$^1$H NMR (400 MHz, Chloroform-d) δ 7.50 (d, J=7.1 Hz, 1H), 7.16-7.29 (m, 12H), 6.96 (t, 1H), 6.85 (d, J=7.5 Hz, 1H), 6.74-6.64 (m, 2H), 5.42 (s, 1H), 4.16 (t, 1H), 3.81 (s, 2H), 3.73 (t, 2H), 3.57 (s, 2H), 3.17 (d, J=7.7 Hz, 2H), 2.76 (s, 3H), 2.73 (t, 2H), 1.88 (pentet, 2H). HRMS (ESI) m/z [M+1]$^+$ $C_{34}H_{35}ClF_3N_2O_2^+$ requires 595.2339, found 595.2332.

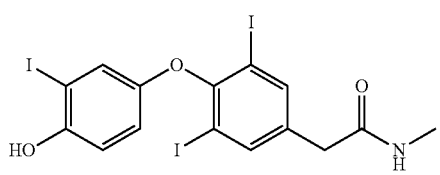 [SMILES: CNC(=O)Cc1cc(I)c(Oc2ccc(O)c(I)c2)c(I)c1]

NRMA-1

2-(4-(4-hydroxy-3-iodophenoxy)-3,5-diiodophenyl)-N-methylacetamide 35 mg triac (0.056 mmol) yielded 30.45 mg (0.048 mmol, 87%) product as an off-white powder.

$^1$H NMR (400 MHz, Chloroform-d) δ 7.78 (s, 2H), 7.10 (dd, J=2.9, 1.1 Hz, 1H), 6.94-6.87 (m, 1H), 6.70 (s, 1H), 3.75 (s, 3H), 3.57 (s, 2H). HRMS (ESI) m/z [M+1]$^+$ $C_{15}H_{13}I_3N_1O_3^+$ requires 635.8024, found 635.8049.

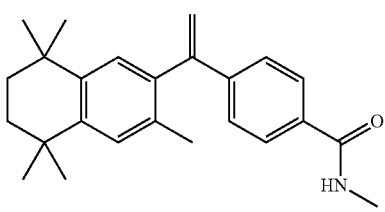 [SMILES: C=C(c1ccc(C(=O)NC)cc1)c1cc2c(cc1C)C(C)(C)CCC2(C)C]

NRMA-4

N-methyl-4-(1-(3,5,5,8,8-pentamethyl-5,6,7,8-tetra-hydronaphthalen-2-yl)vinyl)benzamide 35 mg bexarotene (0.1 mmol) yielded 29.3 mg (0.081 mmol) product as an white powder.
$^1$H NMR (400 MHz, Chloroform-d) δ 7.67 (d, 2H), 7.33 (d, 2H), 7.12 (s, 1H), 7.09 (s, 1H), 6.09 (s, 1H), 5.78 (s, 1H), 5.29 (s, 1H), 3.01 (d, J=4.7 Hz, 3H), 1.93 (s, 3H), 1.69 (s, 4H), 1.30 (s, 6H), 1.27 (s, 6H). HRMS (ESI) m/z [M+1]$^+$ $C_{25}H_{32}N_1O_1^+$ requires 362.2478, found 362.2486.

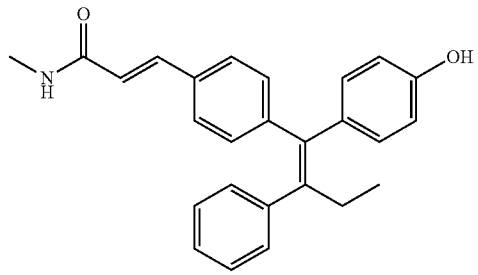 [SMILES: CC/C(=C(\c1ccc(O)cc1)c1ccc(/C=C/C(=O)NC)cc1)c1ccccc1]

NRMA-5

(E)-3-(4-((E)-1-(4-hydroxyphenyl)-2-phenylbut-1-en-1-yl)phenyl)-N-methylacrylamide 35 mg GW7604 (0.094 mmol) yielded 8.3 mg (0.021 mmol, 23%) product as a yellowish residue.
$^1$H NMR (400 MHz, Chloroform-d) δ 7.65 (d, J=15.6 Hz, 1H), 7.44 (m, 1H), 7.24 (m, 2H), 7.20-7.07 (m, 3H), 6.87 (m, 2H), 6.73 (d, J=8.1 Hz, 1H), 6.53 (d, J=8.1 Hz, 1H), 6.40 (d, J=15.5 Hz, 1H), 6.22 (d, J=15.6 Hz, 1H), 5.69 (s, 1H), 5.59 (s, 1H), 2.96 (d, J=19.8 Hz, 3H), 2.52 (q, 2H), 0.95 (t, 3H). HRMS (ESI) m/z [M+1]$^+$ $C_{26}H_{26}N_1O_2^+$ requires 384.1958, found 384.1958.

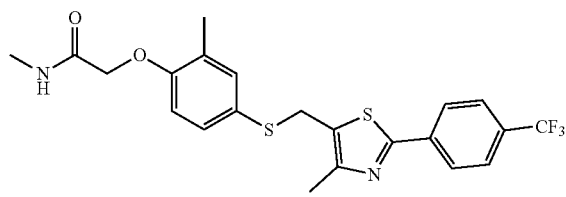 [SMILES: CNC(=O)COc1ccc(SCc2sc(-c3ccc(C(F)(F)F)cc3)nc2C)cc1C]

NRMA-6

N-methyl-2-(2-methyl-4-(((4-methyl-2-(4-(trifluoromethyl)phenyl)thiazol-5-yl)methyl)thio)phenoxy)acetamide 35 mg GW501516 (0.077 mmol) yielded 27.7 mg (0.059 mmol, 77%) product as an off-white powder.
$^1$H NMR (400 MHz, Chloroform-d) δ 7.98 (d, J=8.1 Hz, 2H), 7.67 (d, J=8.2 Hz, 2H), 7.22 (s, 1H), 7.19 (d, 1H), 6.70 (d, J=9.1 Hz, 1H), 6.53 (s, 1H), 4.49 (s, 2H), 4.14 (s, 2H), 2.94 (d, J=5.0 Hz, 3H), 2.24 (s, 3H), 2.22 (s, 3H). HRMS (ESI) m/z [M+1]$^+$ $C_{22}H_{22}F_3N_2O_2S_2^+$ requires 467.1069, found 467.1067.

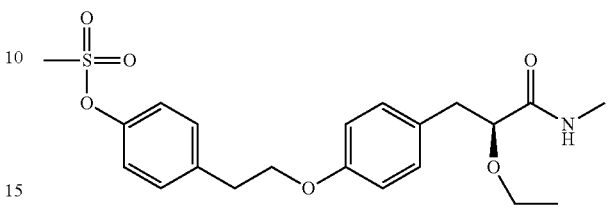

NRMA-7

(S)-4-(2-(4-(2-ethoxy-3-(methylamino)-3-oxopropyl)phenoxy)ethyl)phenyl methanesulfonate 35 mg Tesaglitazar (0.086 mmol) yielded 15.6 mg (0.037 mmol, 43%) product as a yellow oil.
$^1$H NMR (400 MHz, Chloroform-d) δ 7.36 (d, J=8.7 Hz, 2H), 7.28 (d, J=8.7 Hz, 2H), 7.14 (d, J=8.7 Hz, 2H), 6.81 (d, J=8.7 Hz, 2H), 6.48 (s, 1H), 4.16 (t, 2H), 3.91 (m, 1H), 3.44 (m, 1H), 3.13 (s, 3H), 3.11 (m, 2H), 2.86 (m, 1H), 2.79 (d, J=5.0 Hz, 3H), 1.15 (t, 3H). HRMS (ESI) m/z [M+1]$^+$ $C_{21}H_{28}N_1O_6S_1^+$ requires 422.1632, found 422.1638.

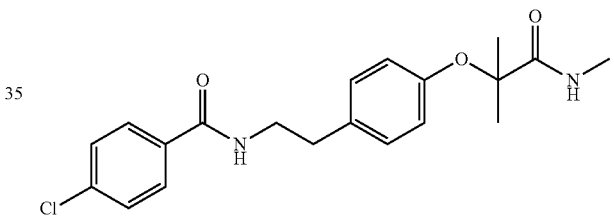

NRMA-8

4-chloro-N-(4-((2-methyl-1-(methylamino)-1-oxopropan-2-yl)oxy)phenethyl)benzamide 35 mg Bezafibrate (0.097 mmol) yielded 29.8 mg (0.079 mmol, 82%) product as a white powder.
$^1$H NMR (400 MHz, Chloroform-d) δ 7.63 (d, J=8.6 Hz, 2H), 7.38 (d, J=8.6 Hz, 2H), 7.12 (d, J=8.5 Hz, 2H), 6.86 (d, J=8.5 Hz, 2H), 6.76 (s, 1H), 6.21 (s, 1H), 3.67 (q, J=6.1 Hz, 2H), 2.90 (m, 2H), 2.88 (s, 3H), 1.48 (s, 6H). HRMS (ESI) m/z [M+1]$^+$ $C_{20}H_{24}ClN_2O_3^+$ requires 375.1470, found 375.1472.

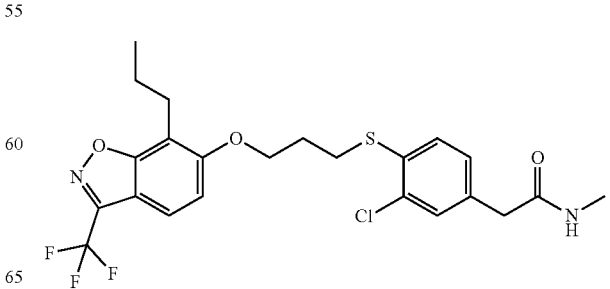

NRMA-9

2-(3-chloro-4-((3-((7-propyl-3-(trifluoromethyl)benzo[d]isoxazol-6-yl)oxy)propyl)thio)phenyl)-N-methylacetamide 35 mg F3MethylAA (0.072 mmol) yielded 11.2 mg (0.022 mmol, 31%) product as a white powder.

$^1$H NMR (400 MHz, Chloroform-d) δ 7.58 (d, J=8.8 Hz, 1H), 7.31 (m, J=3.9 Hz, 2H), 7.15 (d, J=9.9 Hz, 1H), 7.07 (d, J=8.8 Hz, 1H), 5.52 (s, 1H), 4.26 (t, 2H), 3.50 (s, 2H), 3.20 (t, J=7.1 Hz, 2H), 2.94 (t, 2H), 2.80 (d, J=4.8 Hz, 3H), 2.24 (pentet, 2H), 1.72 (sextet, J=7.5 Hz, 2H), 0.98 (t, 3H). HRMS (ESI) m/z [M+1]$^+$ $C_{23}H_{25}ClF_3N_2O_3S_1$+ requires 501.1221, found 501.1218.

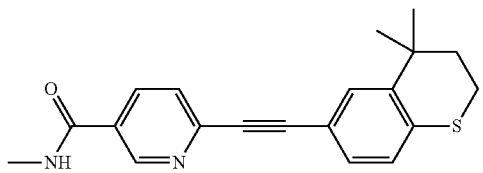 [SMILES: CNC(=O)c1ccc(C#Cc2ccc3c(c2)C(C)(C)CCS3)nc1]

NRMA-10

6-((4,4-dimethylthiochroman-6-yl)ethynyl)-N-methylnicotinamide 35 mg Tazarotenic acid (0.11 mmol) yielded 29.2 mg (0.087 mmol, 79%) product as a yellow powder.

$^1$H NMR (400 MHz, Chloroform-d) δ 8.95 (s, 1H), 8.12 (dd, J=8.1, 2.2 Hz, 1H), 7.64-7.54 (m, 2H), 7.31-7.21 (m, 1H), 7.08 (d, J=8.1 Hz, 1H), 6.54 (s, 1H), 3.10-3.02 (m, 2H), 3.05 (s, 3H), 2.00-1.92 (m, 2H), 1.34 (s, 6H). HRMS (ESI) m/z [M+1]$^+$ $C_{20}H_{21}N_2O_1S_1^+$ requires 337.1369, found 337.1374.

Definitions

The terms "therapeutically effective amount" or "pharmaceutically effective amount" refers to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound described herein, or a pharmaceutically acceptable salt or co-crystal thereof, is an amount sufficient to modulate expression or activity of the intended physiological target, and thereby treat a subject (e.g., a human) suffering an indication, or to ameliorate or alleviate the existing symptoms of the indication. For example, a therapeutically or pharmaceutically effective amount may be an amount sufficient to decrease a symptom of a disease or condition responsive to inhibition of the intended physiological activity.

"Treatment" or "treating" is an approach for obtaining beneficial or desired results including clinical results. Beneficial or desired clinical results may include one or more of the following: (i) inhibiting the disease or condition (e.g., decreasing one or more symptoms resulting from the disease or condition, and/or diminishing the extent of the disease or condition); (ii) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (iii) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Pharmaceutically acceptable salts" include, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesulfonate (besylate), p-toluenesulfonate (tosylate), 2-hydroxyethylsulfonate, benzoate, salicylate, stearate, and alkanoate (such as acetate, HOOC—(CH.sub.2).sub.n—COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

"Subject" refers to an animal, such as a mammal, that has been or will be the object of treatment, observation or experiment. The methods described herein may be useful in both human therapy and veterinary applications. In some embodiments, the subject is a mammal; in some embodiments the subject is human; and in some embodiments the subject is chosen from cats and dogs. "Subject in need thereof" or "human in need thereof" refers to a subject, such as a human, who may have or is suspected to have diseases or conditions that would benefit from certain treatment; for example treatment with a compound described herein, or a pharmaceutically acceptable salt or co-crystal thereof, as described herein. This includes a subject who may be determined to be at risk of or susceptible to such diseases or conditions, such that treatment would prevent the disease or condition from developing.

As used herein, "pharmaceutically acceptable excipient" is a pharmaceutically acceptable vehicle that includes, without limitation, any and all carriers, solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "carrier" refers to an excipient or vehicle that includes without limitation diluents, disintegrants, precipitation inhibitors, surfactants, glidants, binders, lubricants, and the like with which the compound is administered. Carriers are generally described herein and also in "Remington's Pharmaceutical Sciences" by E. W. Martin.

Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

Pharmaceutical Compositions and Administration

Compounds described herein, or a pharmaceutically acceptable salt or co-crystal thereof, are usually administered in the form of pharmaceutical compositions. This disclosure therefore provides pharmaceutical compositions that contain, as the active ingredient, one or more of the compounds described, or a pharmaceutically acceptable salt, pharmaceutically acceptable co-crystal or pharmaceutically acceptable ester thereof, and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compounds described herein, or a pharmaceutically acceptable salt or co-crystal thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In some embodiments, for parenteral administration, sterile injectable solutions are prepared containing a therapeutically effective amount, e.g., 0.1 to 1000 mg, of the compound described herein, or a pharmaceutically acceptable salt or co-crystal thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the compound described herein, or a pharmaceutically acceptable salt or co-crystal thereof. Administration may be via capsule or enteric coated tablets, or the like. In making the pharmaceutical compositions that include the compound described herein, or a pharmaceutically acceptable salt or co-crystal thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, for parenteral administration, each dosage unit contains from 0.1 mg to 1 g, 0.1 mg to 700 mg, or 0.1 mg to 100 mg of a compound described herein, or a pharmaceutically acceptable salt or co-crystal thereof.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of the compound described herein, or a pharmaceutically acceptable salt or co-crystal thereof. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions comprising the compound described herein, or a pharmaceutically acceptable salt or co-crystal thereof, may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Articles of Manufacture and Kits

Compositions (including, for example, formulations and unit dosages) comprising a compound described herein, or a pharmaceutically acceptable salt or co-crystal thereof, can be prepared and placed in an appropriate container, and labeled for treatment of an indicated condition. Accordingly, provided is also an article of manufacture, such as a container comprising a unit dosage form of the compound, or a pharmaceutically acceptable salt or co-crystal thereof, and a label containing instructions for use of the compounds. In some embodiments, the article of manufacture is a container comprising a unit dosage form of the compound of Formula I, or a pharmaceutically acceptable salt or co-crystal thereof, and at least one pharmaceutically acceptable vehicle. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions. It should be understood that the active ingredient may be packaged in any material capable of improving chemical and physical stability, such as an aluminum foil bag. In some embodiments, diseases or conditions indicated on the label can include, for example, treatment of cancer.

Any pharmaceutical composition provided in the present disclosure may be used in the articles of manufacture, the same as if each and every composition were specifically and individually listed for use in an article of manufacture.

Also provided are individual kits, each including a compound described herein, or a pharmaceutically acceptable salt, pharmaceutically acceptable co-crystal, pharmaceutically acceptable ester, stereoisomer, mixture of stereoisomers or tautomer thereof. The kit may comprise a label and/or instructions for use of the compound in the treatment of a disease or condition in a subject (e.g., human) in need thereof.

Sample Collection and Processing

Animal Studies

Experimental protocols were in compliance with the National Institutes of Health Guide for the Care and Use of Laboratory Animals and approved by the Oregon Health & Science University Institutional Animal Care & Use Committee. *Wild type* male C57Bl/6 mice, aged 8-10 weeks, were housed in a climate-controlled room with a 12-h light-dark cycle with ad libitum access to food and water. Mice were injected once intraperitoneally (i.p.) with parent drug or prodrug at 9.14 μmol/kg. Euthanasia was performed on three mice per time point at the following times: 0.5 h, 2 h, and 6 h (except where noted otherwise) and the tissues and blood were harvested. Tissues were immediately frozen and blood was kept on ice for a minimum of 30 min and then spun down at 7500×g for 15 min. Serum (100 μL) was collected and was stored with tissues at −80° C. until samples were processed.

Serum Processing

The serum samples were warmed to r.t. and 10 μL of 2.99 μM internal standard (d-sobetirome) was added to them. Acetonitrile (500 μL) was added and the sample was vortexed for 20 s. The sample was then centrifuged at 10,000 g for 15 min at 4° C. Next, 90% of the upper supernatant was transferred to a glass test tube and concentrated using a speedvac for 1.5 h at 45° C. The dried sample was then dissolved in 400 μL of 10% DMF in ACN and vortexed for 20 s. The resulting mixture was transferred to an eppendorf and centrifuged at 10,000 g for 15 min. The supernatant was filtered with 0.22 μm centrifugal filters and submitted for LC-MS/MS analysis. Standard curves were made with 100 μL of serum from an 8-10 week old mouse injected with vehicle (DMSO) only. The processing was performed exactly the same except after filtering the sample was split amongst 7 vials. To 6 out of the 7 vials was added parent drug to make final concentrations in matrix of (0.1 pg/μL, 0.5 pg/μL, 1 pg/μL, 10 pg/μL, 100 pg/μL, and 500 pg/μL).

Brain Processing

The brain samples were warmed to r.t. and transferred to a preweighed homogenizer tube containing 3 GoldSpec 1/8 chrome steel balls (Applied Industrial Technologies). The resulting tube was weighed and then 1 mL of $H_2O$ was added, followed by 10 μL of 2.99 μM internal standard ($d_6$-sobetirome). The tube was homogenized with a Bead Bug for 30 s and then transferred to a falcon tube containing 3 mL of ACN. ACN (1 mL) was used to wash homogenizer tube and the solution was transferred back to the falcon tube. The sample was then processed using the same method for the serum processing except the sample was concentrated in a glass tube using a speed vac for 4 h at 45° C.

FAAH Inhibition Study

Two cohorts of three mice were injected once intraperitoneally (i.p.) with prodrug at 9.14 μmol/kg. One cohort was injected 1 h prior to prodrug administration with a 1 mg/kg dose of FAAH inhibitor PF-3845. Euthanasia was performed on each cohort 1 h after injection with the prodrug and the tissues and blood were harvested. Tissues were immediately frozen and blood was kept on ice for a minimum of 30 min and then spun down at 7500×g for 15 min. Serum (100 L) was collected and was stored with tissues at −80° C. until samples were processed. Samples were processed as described above.

LC-MS/MS Analysis for Parent Drugs and Prodrugs

All parent drugs and d6-sobetirome internal standard were analyzed using a QTRAP 4000 hybrid/triple quadrupole linear ion trap mass spectrometer (Applied biosystems) with electrospray ionization (ESI) in negative mode. The mass spectrometer was interfaced to a Shimadzu (Columbia, Md.) SIL-20AC XR auto-sampler followed by 2 LC-20AD XR LC pumps and analysis on an Applied Biosystems/SCIEX QTRAP 4000 instrument (Foster City, Calif.). The instrument was operated with the following settings: source voltage −4500 kV, GS150, GS2 60, CUR 15, TEM 650, and CAD MEDIUM. The scheduled multiple-reaction-monitoring (MRM) transitions are based on the precursor ion m/z and their corresponding diagnostic product ions. Compounds were infused individually and instrument parameters optimized for each MRM transition. MRM parameters are shown in the Supporting Supporting information. The gradient mobile phase was delivered at a flow rate of 0.5 mL/min, and consisted of two solvents, A: 10 mM ammonium formate in water and B: 10 mM ammonium formate in 90% acetonitrile, 10% water. An Imtakt Scherzo SS-C18 50×2 mm 3 μm (prod #SS022) was used with an Imtakt Guard cartridge Scherzo SS-C18 5×2 mm 3 μm precolumn (prod #GCSSOS) and kept at 40° C., and the autosampler was kept at 30° C. Gradient was as follows, initial concentration of B was 10%, held for 0.5 min, followed by an increase to 98% B over 4.5 min, held for 0.9 min, dropping back to 10% B over 0.1 min, and held at 10% B for 2 min for a total run time of 8 min. Data were acquired using SCIEX Analyst 1.6.2 software (Framingham, Mass., USA) and analyzed using Multiquant 3.0.2

Statistics

Statistical analyses were performed using the two-tailed Student t test comparing individual groups with the appropriate vehicle group or as noted. Significance level was set to <0.05 with P values illustrated with the following symbols: ns=not significant, *P≤0.05, P≤0.01, and *P≤0.001. All data represent mean±SEM. Animal group numbers were informed by previous work to minimize total animal numbers as appropriate per experiment. AUC values were calculated and data was plotted and analyzed using GraphPad Prism 7.

Figure 16:
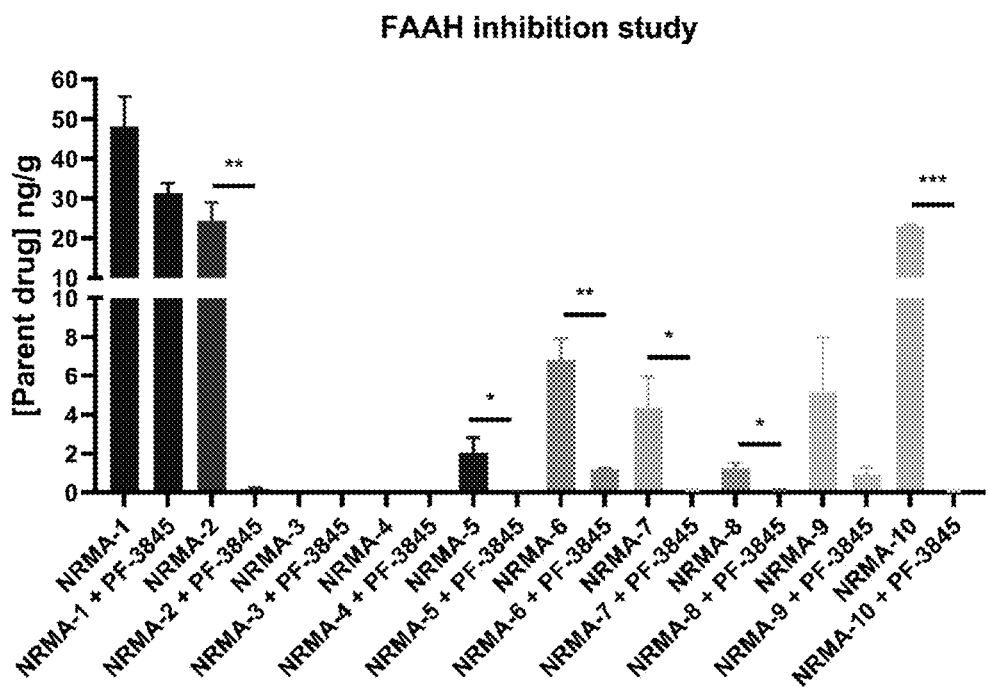
FIG. 16 provides a comparison of FAAH inhibition for compounds and combinations tested.

FIG. 16 provides a comparison between mouse cohorts (n=3) dosed with either prodrug or prodrug with global FAAH inhibitor PF-3845 given 1 h prior to administration of prodrug. In all cases, prodrug administration in the absence of FAAH inhibitor delivers more parent drug to the brain at the 1 h post-dose timepoint. Most comparisons yield a statistical difference between same-prodrug cohorts which suggests that delivery of the parent drug to the brain operates via FAAH cleavage of the prodrug.

TABLE 1

Table of parent drug and prodrug AUC values

| Compound (9.14 mmol/kg, ip) | Brain $AUC_{0.5-6\,h}$ (ng/g*h) | Serum $AUC_{0.5-6\,h}$ (ng/g*h) | Brain/Serum Ratio |
|---|---|---|---|
| Triac | 88.9 | 5108 | 0.017 |
| NRMA-1 | 155.8 | 4020 | 0.039 |
| NH-3 | 11.9 | 756.9 | 0.016 |
| NRMA-2 | 73.8 | 49.5 | 1.5 |
| GW501516 | 41.8 | 2330 | 0.018 |
| NRMA-6 | 146.3 | 2705 | 0.054 |
| Tesaglitazar | 7.3 | 2107 | 0.004 |
| NRMA-7 | 21.9 | 374.1 | 0.06 |
| Bezafibrate | 5.5 | 420.7 | 0.013 |
| NRMA-8 | 26.3 | 470.6 | 0.06 |
| Tazarotenic acid | 38.5 | 314.5 | 0.12 |
| NRMA-10 | 104 | 51.34 | 2.03 |

Table 2 depicts the Brain AUCs, Serum AUCs, and Brain/Serum Ratios of three drugs and their corresponding methyl amide prodrug.

TABLE 2

| Compound (9.14 mmol/kg, ip) | Brain AUC | Serum AUC | Brain/Serum Ratio |
|---|---|---|---|
| NH-3 | 11.9 | 756.9 | 0.016 |
| NH-3 prodrug | 73.8 | 49.5 | 1.5 |
| Tesaglitazar | 7.3 | 2107 | 0.004 |
| Tesaglitazar prodrug | 21.9 | 374.1 | 0.06 |
| Bexarotene | 665.5 | 639 | 1.04 |
| Bexarotene prodrug | 1.6 | 1.7 | 0.9 |

Table 3 depicts the Brain AUCs, Serum AUCs, and Brain/Serum Ratios of NH3, NH-3 prodrug, and Tesaglitazar.

TABLE 3

| Compound (9.14 mmol/kg, ip) | Brain AUC (ng/g*h) | Serum AUC (ng/g*h) | Brain/Serum Ratio |
|---|---|---|---|
| NH-3 | 11.9 | 756.9 | 0.016 |
| NH-3 prodrug | 73.8 | 49.5 | 1.5 |
| Tesaglitazar | 7.3 | 2107 | 0.004 |

What is claimed:
1. A compound:

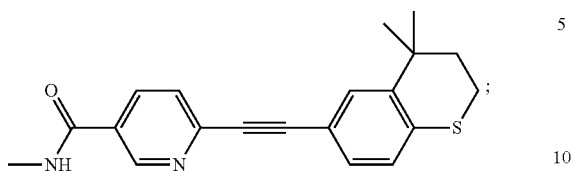

or a pharmaceutically acceptable salt thereof.

2. A pharmaceutical composition comprising a pharmaceutically effective amount of the compound of claim 1, or a pharmaceutically acceptable salt thereof, and a pharmaceutically acceptable carrier or excipient.

3. A method of treating a neurodegenerative disorder in a subject in need thereof comprising administering to the subject a pharmaceutically effective amount of the compound of claim 1, or a pharmaceutically acceptable salt thereof.

* * * * *